US005876345A

United States Patent [19]
Eaton et al.

[11] Patent Number: 5,876,345
[45] Date of Patent: Mar. 2, 1999

[54] ULTRASONIC CATHETER, SYSTEM AND METHOD FOR TWO DIMENSIONAL IMAGING OR THREE-DIMENSIONAL RECONSTRUCTION

[75] Inventors: John W. Eaton; John A. Hossack, both of Palo Alto, Calif.

[73] Assignee: Acuson Corporation, Mountain View, Calif.

[21] Appl. No.: 807,621

[22] Filed: Feb. 27, 1997

[51] Int. Cl.⁶ .................................................. A61B 8/00
[52] U.S. Cl. ........................................ 600/466; 600/463
[58] Field of Search .................................. 680/466, 447; 128/916; 600/462, 467

[56] References Cited

U.S. PATENT DOCUMENTS

| | | |
|---|---|---|
| Re. 30,397 | 9/1980 | King . |
| 4,140,022 | 2/1979 | Maslak . |
| 4,241,608 | 12/1980 | Dees et al. . |
| 4,635,293 | 1/1987 | Watanabe . |
| 4,841,977 | 6/1989 | Griffith et al. . |
| 4,917,097 | 4/1990 | Proudian et al. . |
| 4,937,775 | 6/1990 | Engeler et al. . |
| 4,947,852 | 8/1990 | Nassi et al. ............................ 600/466 |
| 5,000,185 | 3/1991 | Yock ..................................... 600/466 |
| 5,014,710 | 5/1991 | Maslak et al. . |
| 5,070,879 | 12/1991 | Herres . |
| 5,081,993 | 1/1992 | Kitney et al. . |
| 5,103,129 | 4/1992 | Slayton et al. . |
| 5,107,844 | 4/1992 | Kami et al. . |
| 5,127,409 | 7/1992 | Daigle . |
| 5,159,931 | 11/1992 | Pini . |
| 5,161,537 | 11/1992 | Hashimoto et al. . |
| 5,186,176 | 2/1993 | Hiki et al. . |
| 5,186,177 | 2/1993 | O'Donnell et al. . |
| 5,199,437 | 4/1993 | Langberg . |
| 5,211,176 | 5/1993 | Ishiguro et al. . |
| 5,257,629 | 11/1993 | Kitney et al. . |
| 5,273,045 | 12/1993 | Chihara et al. . |

(List continued on next page.)

OTHER PUBLICATIONS

Rosenfiedl et al., Three–Dimensional Reconstruction of Human Coronary and Peripherial Arteries from Images Recorded During Two–Dimensional Intravascular Ultrasound Examination, Corculation, vol. 84, No. 5, pp. 1938–1956, Nov. 1991.

"Early and Recent Intraluminal Ultrasound Devices, " N. Bom et al., International Journal of Cardiac Images 4, pgs. 79–88. (1989).

Laurence N. Bohns et al., "A Novel Method For Angle Independent Ultrasonic Imaging of Blood Flow and Tissue Motion," (1991).

A. Shaulov et al., "Biplane Phased Array for Ultrasonic Medical Imaging," (1988), pp. 635–638.

Timothy C. Hodges et al., "Ultrasonic Three–Dimensional Reconstruction: In Vitro and In Vivo Volume and Area Measurement, "(1994), pp. 719–729.

Hugh A. McCann et al., "Multidimensional Ultransonic Imaging for Cardiology, "(1988), pp. 1063–1072.

Elizabeth O. Ofili et al., "Three–Dimensional and Four–Dimensional Echocardiogrphy, "(1994), pp. 669–675.

J. Souquet et al., "Transesphageal Phased Array for Imaging the Heart, " (1982), pp. 707–712.

*LSI Logic*,Appendix 2, "L64720 Video Motion Estimation Processor (MEP), "1 page.

*ISO/IEC Standard (MPEG Video)*, "Introduction –Part 2: Video, "(1991) pp. 5–9.

(List continued on next page.)

*Primary Examiner*—Marvin M. Lateef
*Assistant Examiner*—Maulin Patel
*Attorney, Agent, or Firm*—Brinks Hofer Gilson & Lione

[57] ABSTRACT

An ultrasonic catheter having at least two ultrasonic arrays is provided which has good near and far field resolution and provides an outline of the heart chamber which assists in understanding and interpreting the images obtained by the catheter. Also the ultrasonic catheter allows three dimensional images to be constructed of the region examined by the catheter in a precise but facile manner.

75 Claims, 8 Drawing Sheets

U.S. PATENT DOCUMENTS

| | | |
|---|---|---|
| 5,315,512 | 5/1994 | Roth . |
| 5,325,860 | 7/1994 | Seward et al. . |
| 5,327,895 | 7/1994 | Hashimoto et al. . |
| 5,345,940 | 9/1994 | Seward et al. . |
| 5,353,354 | 10/1994 | Keller et al. . |
| 5,368,037 | 11/1994 | Eberle et al. . |
| 5,377,682 | 1/1995 | Ueno et al. ............................ 600/466 |
| 5,398,691 | 3/1995 | Martin et al. . |
| 5,456,259 | 10/1995 | Barlow et al. . |
| 5,469,851 | 11/1995 | Lipschutz . |
| 5,471,988 | 12/1995 | Fujio et al. . |
| 5,487,388 | 1/1996 | Rello et al. . |
| 5,492,125 | 2/1996 | Kim et al. . |
| 5,497,776 | 3/1996 | Yamazaki et al. . |
| 5,503,153 | 4/1996 | Liu et al. . |
| 5,517,537 | 5/1996 | Greene et al. . |
| 5,529,070 | 6/1996 | Augustine et al. . |
| 5,538,004 | 7/1996 | Bamber . |
| 5,558,091 | 9/1996 | Acker et al. . |
| 5,566,674 | 10/1996 | Weng . |
| 5,570,691 | 11/1996 | Wright et al. . |
| 5,575,286 | 11/1996 | Weng et al. . |
| 5,582,173 | 12/1996 | Li . |
| 5,590,654 | 1/1997 | Hamilton et al. ....................... 600/447 |
| 5,606,975 | 3/1997 | Liang et al. ........................... 600/462 |
| 5,608,849 | 3/1997 | King, Jr. . |
| 5,699,805 | 12/1997 | Seward et al. . |
| 5,704,361 | 1/1998 | Seward et al. . |
| 5,713,363 | 2/1998 | Seward et al. . |
| 5,724,978 | 3/1998 | Tenhoff .................................... 128/916 |
| 5,776,067 | 7/1998 | Kamada et al. . |

OTHER PUBLICATIONS

Shinichi Tamura et al., "Three Dimensional Reconstruction of Echocardiograms Based on Orthogonal Sections, "(1985) pp. 115–124.

Frederich Dohery, M.D. et al., "SONOLINE ®Elegra Ultrasound Imaging Platform and Extended Field of View XFOV™Imaging," (1995), 4pages.

M. Belohlavek et al., "Multidimensional Ultrasonic Visualization in Cardiology," (1992) 1137–1145.

Dan Sapoznikov et al., "Left Ventricular Shape, Wall Thickness and Function Based on Three–Dimensional", pp. 195, 496–498.

U.S. application No. 08/874,792, Seward et al., filed Jun. 13, 1997.

O'Donnell, M., et al., "Synthetic Phased Array Imaging of Coronary Arteries with an Intraluminal Array, "IEEE Ultrasonics Symposium, pp. 1251–1254 (1995).

Gussenhoven, E. et al., "Displacement Sensing Device Enabling Accurate Documentation of Catheter Tip Position," Intravascualar Ultrasound, pp. 157–166 (1993).

One page product brochure of Powerpace Enhancement Package, (date unknown).

Two page B&K Medical product brochure describing B&K 8558 transducer and B&K 8557 transducer, (date unknown).

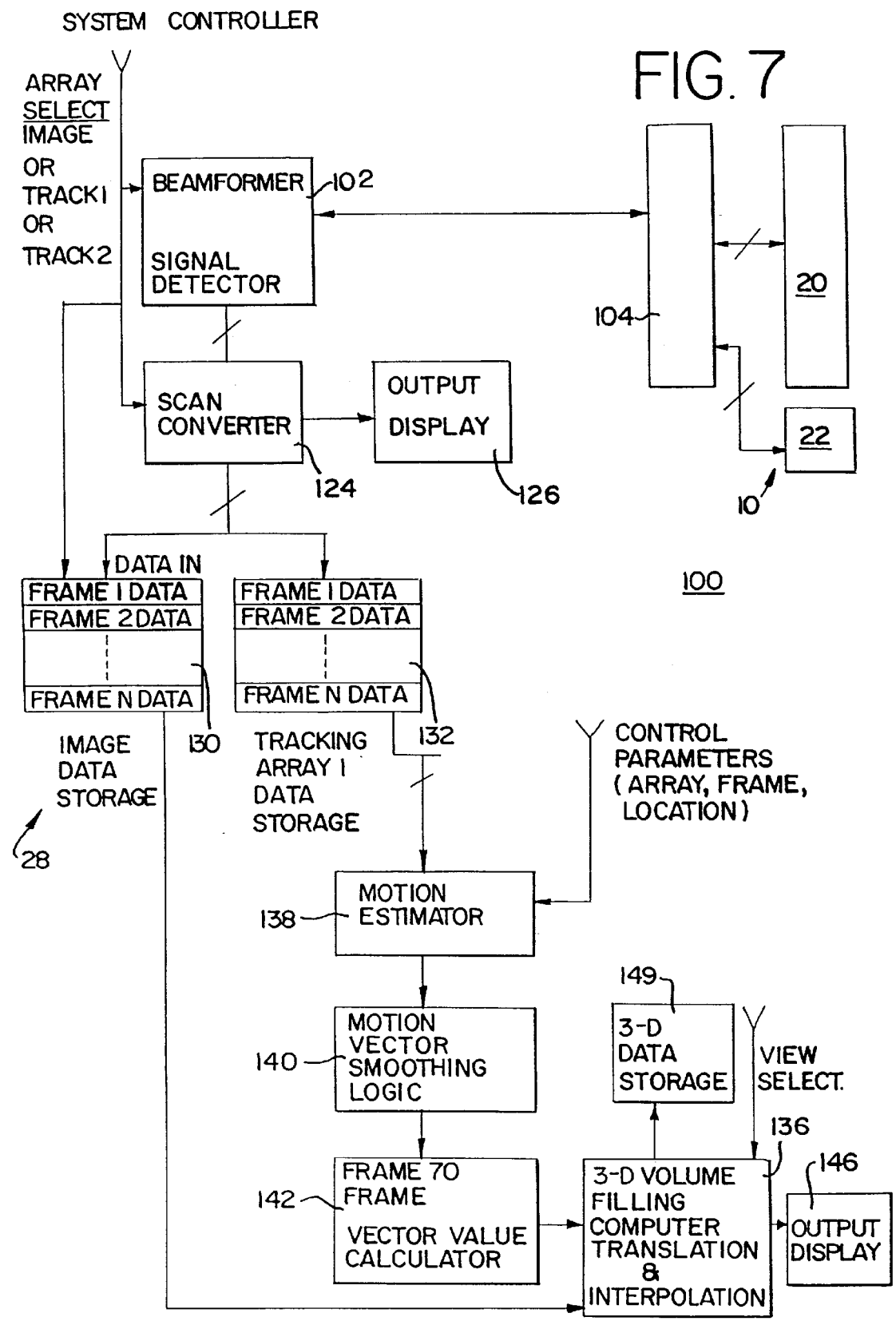

ULTRASONIC CATHETER, SYSTEM AND METHOD FOR TWO DIMENSIONAL IMAGING OR THREE-DIMENSIONAL RECONSTRUCTION

FIELD OF THE INVENTION

This invention relates to an ultrasonic catheter, system and method for acquiring two-dimensional image information and relative positional information to allow subsequent three dimensional reconstruction utilizing a catheter that has at least two ultrasonic transducer arrays which generate differing image formats mounted thereon.

BACKGROUND OF THE INVENTION

Catheter-mounted ultrasonic transducers have in the past taken several forms, including (1) single-element transducer crystals that are pointed radially outward and rotated about the axis of the catheter, (2) radial phased array transducers and, (3) linear array transducers. For example, Bom U.S. Pat. No. 3,958,502 discloses a catheter with a radial phased ultrasonic array arranged circumferentially around the axis of the catheter. Proudian U.S. Pat. No. 4,917,097 describes a similar catheter with a radial phased ultrasonic array (and alludes to other geometries). Other catheters with radial phased ultrasonic arrays are described in Griffith et al. U.S. Pat. No. 4,841,977; O'Donnell et al. U.S. Pat. No. 5,186,177; and Barlow et al. U.S. Pat. No. 5,456,259. Seward et al. (Seward, J. B., D. L. Packer, R. C. Chan, M. G. Curley, A. J. Tajik (1996)), "Ultrasound Cardioscopy: Embarking on a New Journey," Mayo Clinic Proceedings, 71(7)) describe a catheter having a linear phased ultrasonic array for insertion into the heart. Eberle et al. U.S. Pat. No. 5,368,037 describes a catheter that has an ultrasound transducer array according to several embodiments. In one embodiment the array is configured as a cylinder about a cylindrical core (see FIG. 1 of the '037 patent), in another embodiment the transducer array is a side fire, side-looking linear array (see FIGS. 7A and 7B of the '037 patent) and in another embodiment the transducer array is an end fire, forward-looking array (see FIGS. 8A–C of the '037 patent).

Thus, with respect to known catheters, which incorporate ultrasonic transducer technology, only one type of transducer array is incorporated in the catheter, whether it be a radial phased array, a linear array or single crystal design.

While radial phased transducers provide good near field resolution, i.e. about 1–5 cm, a disadvantage of catheters that utilize a radial phased array is that the radial phased image format generated by the array does not have the diagnostic image resolution or penetration that a linear phased array can produce. In addition, radial phased imaging devices cannot image across the heart to opposite chambers or image larger cardiac structures or image far beyond the vessel it is placed in.

Conversely, while catheters having linear phased arrays have good resolution in the near and far fields, i.e., up to about 12 cm, and are able to image across the heart to opposite chambers, or across vessels to other organs, the location of an image plane is sometimes difficult to interpret.

Thus, it is desirable to provide a catheter incorporating ultrasonic transducer technology that allows good near and far field resolution while accurately depicting the location in the heart or vessel.

In addition, catheters that utilize a single type of ultrasonic transducer array only provide two dimensional information of the region examined by the catheter. Attempts have been made to construct three dimensional images using a catheter with a linear ultrasonic array by collecting multiple two dimensional image data frames using the array mounted on the catheter along with relative positional information among the image data frames so that these image frames may be subsequently assembled into a three dimensional volume to form the desired three dimensional reconstruction. The relative positional information is acquired by externally rotating the catheter while trying to maintain angular control. Such manual techniques are slow and cumbersome and therefore have many drawbacks.

One approach is described in the article by Gussenhoven et al., entitled "Displacement Sensing Device Enabling Accurate Documentation of Catheter Tip Position," *Intravascular Ultrasound*, pg. 157–166 (1993), involves incrementally inserting a catheter having a radial scanning array into a region of interest to acquire multiple spaced two dimensional radial scans while monitoring the incremental increase in depth of penetration by passing the catheter between rollers which are attached to rotary encoders. The inclusion of mechanical sensing devices, however, compromises reliability of the measurements. In addition, the rollers may slip against the surface of the catheter thereby introducing error in the measurements.

Thus it is also desirable to provide a catheter that incorporates ultrasonic transducer technology that allows three dimensional images to be constructed of the region examined by the catheter in a precise but facile manner.

SUMMARY OF THE INVENTION

According to a first aspect of the present invention there is provided an ultrasonic catheter having a body having a longitudinal axis, a circumference and a distal end region, a first ultrasonic transducer array disposed in the distal end region of the body, and a second ultrasonic transducer array disposed in the distal end region of the body.

According to a second aspect of the present invention there is provided an ultrasonic system having an ultrasonic catheter including a body having a longitudinal axis, a circumference and a distal end region. The ultrasonic catheter includes a first ultrasonic transducer array disposed in the distal end region of the body and a second ultrasonic transducer array disposed in the distal end region of the body. A transmit beamformer and a receive beamformer are coupled to each of the first and second ultrasonic transducer arrays.

According to a third aspect of the present invention there is provided a method for registering image information acquired from an interior region of a patient. The method includes the steps of:

(a) inserting a catheter having a body having a longitudinal axis, a circumference and a distal end region, a first ultrasonic transducer array disposed in the distal region of the body and a second phased ultrasonic transducer array disposed around the circumference of the distal end region of the body into a patient to image an interior region of the patient;

(b) acquiring first two-dimensional image information in an image plane with the first ultrasonic transducer array;

(c) acquiring tracking two-dimensional data information in a tracking plane oriented at a non-zero angle with respect to the image plane with the second ultrasonic transducer array;

(d) repeating steps (b) and (c) after moving the catheter along a direction having a component of motion in the tracking plane;

(e) automatically determining the component of motion based on a comparison of the tracking two-dimensional data information acquired in steps (c) and (d); and (f) automatically using the component of motion determined in step (e) to register the first image information acquired in step (d) with the first image information acquired in step (b).

According to a fourth aspect of the present invention there is provided a method for imaging a cardiac structure. The method includes the steps of:

(a) inserting a catheter having a body having a longitudinal axis, a circumference and a distal end region with a linear phased ultrasonic transducer array and a radial phased ultrasonic transducer array disposed thereon;

(b) acquiring image information from the linear phased ultrasonic transducer array; and (c) acquiring image information from the radial phased ultrasonic transducer array.

According to a fifth aspect of the present invention there is provided a method for registering image information acquired from an interior region of a patient. The method includes the steps of:

(a) inserting an catheter having a body having a longitudinal axis, a circumference and a distal end region, a linear phased ultrasonic transducer array disposed in the distal region of the body and a first radial phased ultrasonic transducer array disposed around the circumference of the distal end region of the body into a patient to image an interior region of the patient;

(b) acquiring first two-dimensional image information in an image plane with the radial phased ultrasonic transducer array;

(c) acquiring tracking two-dimensional data information in a tracking plane oriented at a non-zero angle with respect to the image plane with the linear phased ultrasonic transducer array;

(d) repeating steps (b) and (c) after moving the catheter along a direction having a component of motion in the tracking plane;

(e) automatically determining the component of motion based on a comparison of the tracking two-dimensional data information acquired in steps (c) and (d); and (f) automatically using the component of motion determined in step (e) to register the first image information acquired in step (d) with the first image information acquired in step (b).

BRIEF DESCRIPTION OF THE DRAWINGS

FIG. 7 is a block diagram of an ultrasonic system according to a preferred embodiment of the present invention.

FIG. 16 illustrates the distal region of still another preferred embodiment of a catheter according to the present invention.

DETAILED DESCRIPTION OF THE PRESENTLY PREFERRED EMBODIMENTS

Figure 1:
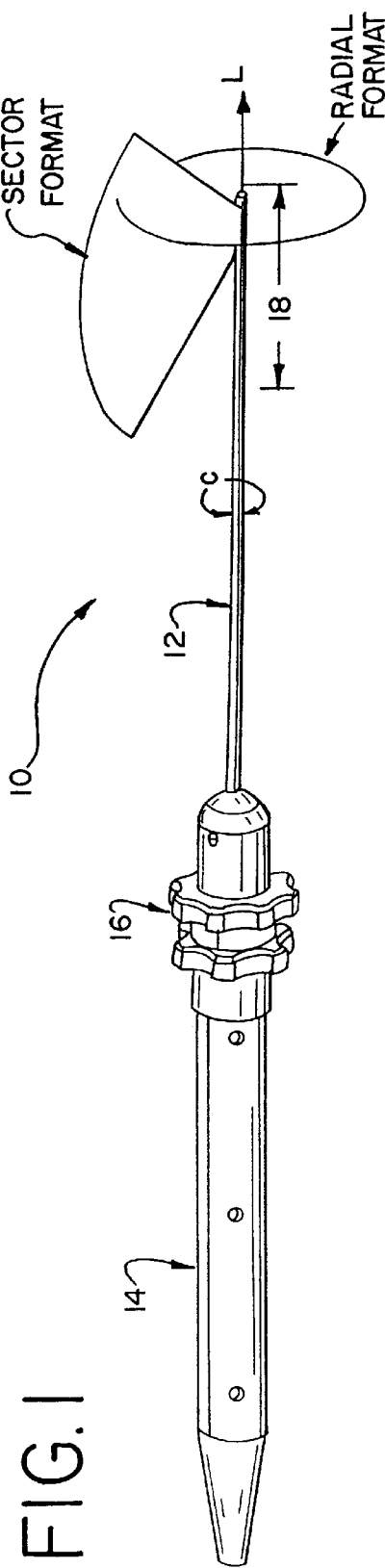
FIG. 1 is a schematic view of a catheter according to a preferred embodiment of the present invention.

FIG. 1 is a schematic view of a catheter 10 according to a preferred embodiment of the present invention. The catheter 10 includes a body 12, handle 14 and a steering mechanism 16 which couples the proximal end of the body 12 to the handle 14. The handle 14 and steering mechanism 16 are well known in the art and need not be described in detail. Preferably, the catheter incorporates the steering mechanism described in U.S. patent application Ser. No. 08/792,897, entitled "Steering Mechanism and Steering Line For a Catheter-Mounted Ultrasonic Transducer," filed Jan. 31, 1997 (Attorney Docket No. 5050/171) which is assigned to the assignee of this invention, and which is hereby specifically incorporated by reference.

The body 12 is preferably in the form of a flexible shaft having a longitudinal axis L and a circumference C. The body 12 has a distal end region 18 which includes at least two ultrasonic transducer arrays that preferably generate different image formats when operated as will be described in greater detail hereinafter. The distal end region 18 will be described in greater detail with reference to FIGS. 2 and 3.

Preferably the catheter incorporates extended flexible circuits such as described in U.S. patent application Ser. No. 08/791,601, entitled "Ultrasonic Transducer Array With Extended Flexible Circuits," filed Jan. 31, 1997 (Attorney Docket No. 5050/161) assigned to the assignee of this invention, and which is hereby specifically incorporated herein by reference. Also preferably the catheter incorporates an electrical interconnection system such as that described in U.S. patent application Ser. No. 08/792,291, entitled "Ultrasonic Transducer Assembly With Improved Electrical Interface," filed Jan. 31, 1997 (Attorney Docket No. 5050/169) assigned to the assignee of this invention, and which is hereby specifically incorporated herein by reference. Also the distal end of the catheter may be formed according to the teachings of U.S. patent application Ser. No. 08/791,598, entitled "Catheter Mounted Phased Array Ultrasound Transducer With Improved Imagery," filed Jan. 31, 1997 (Attorney Docket No. 5050/170) which is assigned to the assignee of this invention and which is specifically incorporated herein by reference.

The body 12 is preferably constructed of Pebax, manufactured by ELF ATOCHEM North America Inc. of Philadelphia, Pa. and may have a length ranging from about 60 cm to about 120 cm, an inner lumen, and an outer diameter ranging from about 1 mm to about 4 mm.

Figure 2:
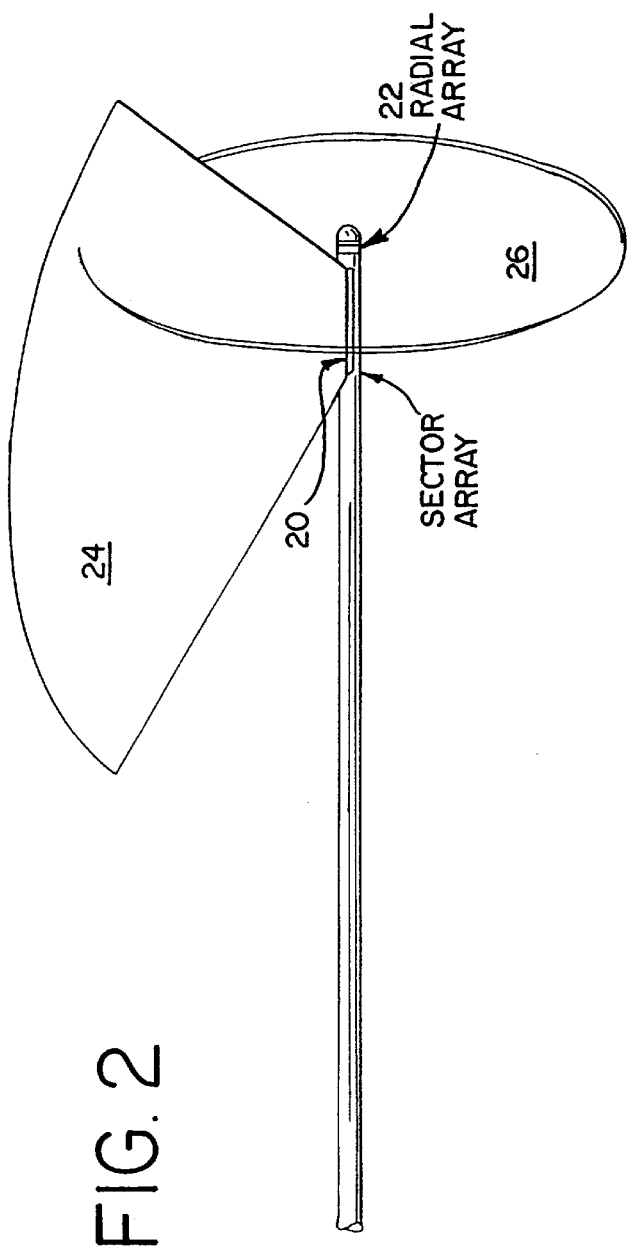
FIG. 2 is a magnified view of the distal end region shown in FIG. 1.
Figure 3:
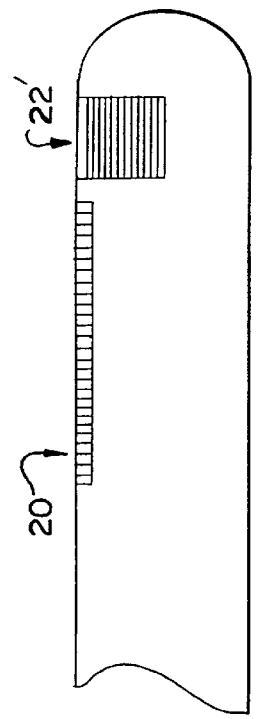
FIG. 3 illustrates a distal end region of a catheter according to a preferred embodiment of the present invention.
Figure 4:
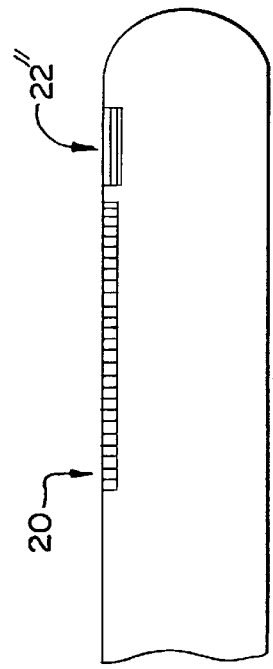
FIG. 4 illustrates a distal end region of a catheter according to a preferred embodiment of the present invention.

FIG. 2 is a magnified view of the distal end region 18 of the body 12 of the catheter 10 shown in FIG. 1. A first ultrasonic transducer array 20 ("first array 20") and a second ultrasonic transducer array 22 ("second array 22") are provided in the distal end region 18 of the catheter 10. In a preferred embodiment the first array 20 is a linear phased array and the second array 22 is a radial phased array. In a preferred embodiment, the radial phased array is an annular array. When the annular array is excited, all of the emitted acoustic lines have a common origin lying at the center of the annular array. An annular array is used to obtain a 360 degree scan. A 360 degree scan, however, is not always necessary for every application. In particular, in another preferred embodiment shown in FIG. 3 the radial array 22' may be formed by a curved linear phased array which does not form an annulus and only provides less than a 360° scan. In another preferred embodiment shown in FIG. 4, the radial array 22" may be formed by a substantially planar linear phased array which provides less than a 360° radial scan. A radial array, as that term is used in the present invention, is any array that generates a scan in a plane perpendicular to the longitudinal axis of the catheter when the array is excited. If the radial array is formed by a linear or curved linear phased array the scan obtained may be linear, sector or VECTOR™ format.

Figure 5:
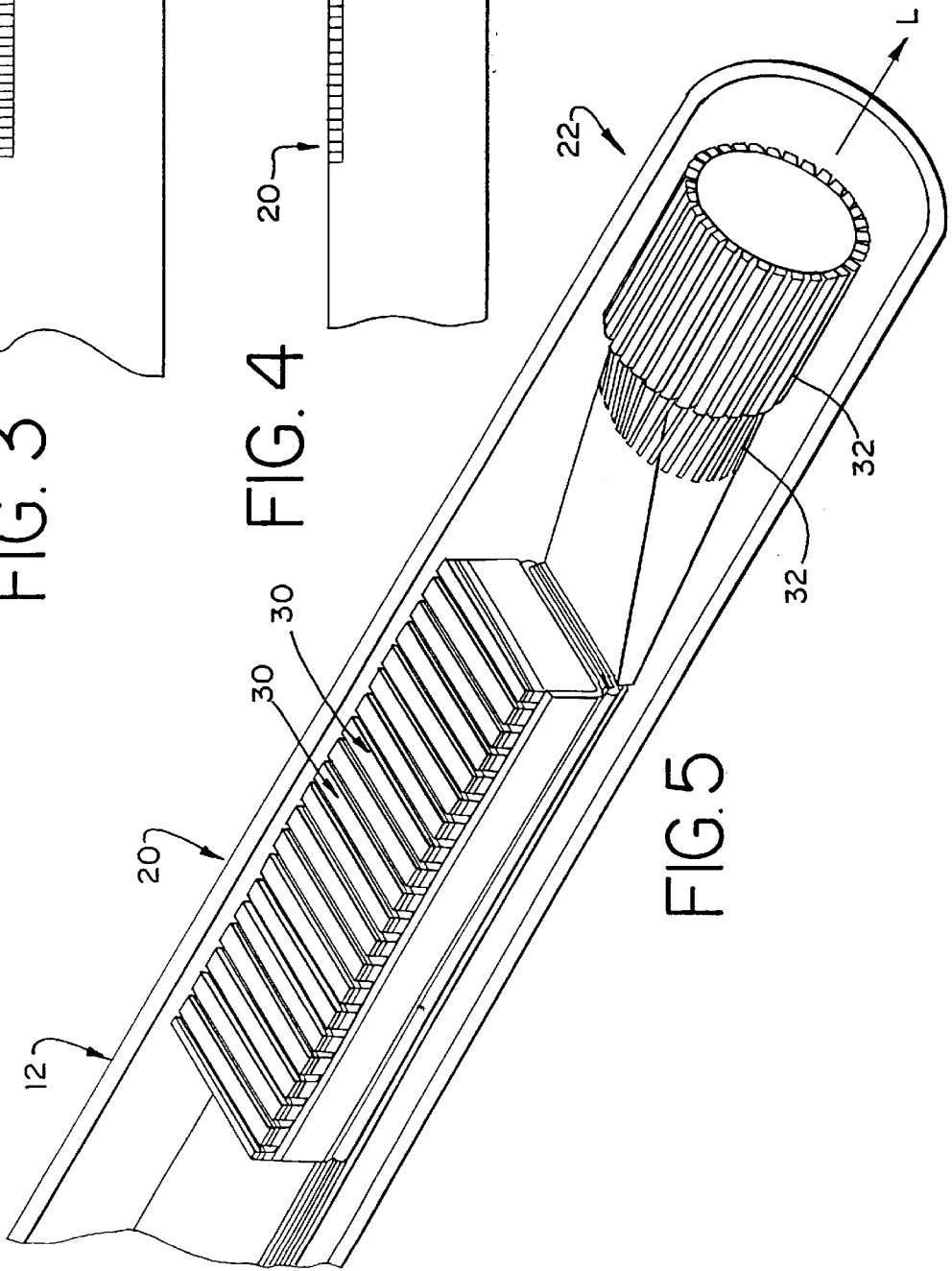
FIG. 5 is a further magnified view of the distal end region shown in FIG. 2.

FIG. 5 is a further magnified view of the distal end region shown in FIG. 2 with a portion of the body 12 removed to better illustrate the arrays. A lens or acoustic window (not shown) may cover the emitting faces of the arrays but has been omitted for purposes of clarity. Linear phased ultrasonic array 20 is formed by a plurality of transducer elements 30 that are sequentially arranged along the longitudinal axis L of the body 12. The azimuth of the array 20 extends parallel with the longitudinal axis L of the body 12. In a preferred embodiment the linear phased array 20 is formed by 64 transducer elements having an elevation dimension extending into the Figure of about 2.5 mm. The transducer elements are preferably spaced on a 0.11 mm pitch. The linear phased array 20 can be of conventional form, such as a flat linear phased array with a cylindrical elevation focusing lens but preferably uses a non-focusing window. All imaging modes including B mode, color Doppler, color Doppler energy and the like are supported. The linear phased array 20 may include more or less than 64 elements and may have a different pitch and elevation.

Radial phased ultrasonic transducer array 22 in FIG. 2 is formed by a plurality of transducer elements 32 sequentially arranged circumferentially so that it is preferably concentric with the body 12. The radial phased array 22 is preferably formed by 64 elements having an elevation dimension of 2.5 mm spaced on a 0.11 mm pitch. In a preferred embodiment the radial phased array 22 is annular to provide a 360° scan. An annular array may be manufactured from an annulus of piezoelectric material or, alternatively, an annular array may be formed by wrapping a flat transducer array that has been partially diced around a backing block support. Alternatively the radial phased array 22 may be formed by fewer elements and thus provide less than a 360° scan.

As is well known in the art, conventional ultrasound transducers are typically constructed of piezoelectric material such as PZT. In a preferred embodiment, the piezoelectric material for arrays 20 and 22 is preferably 3203HD sold by Motorola Ceramics of Albuquerque, N. Mex. Preferably, each transducer element includes two matching layers. The matching layer adjacent to the PZT is an epoxy loaded with alumina or lithium aluminum silicate and/or metal power such as tungsten preferably 325 mesh and possesses an acoustic impedance of approximately 8–10 MRayls. The second matching layer—further from the PZT—is preferably an unfilled epoxy possessing an impedance of approximately 2.5 MRayls. The arrays 20 and 22 are constructed using well known techniques which involve laminating the matching layers, an electroded slab of PZT and a flexible circuit onto a thin backing block substrate. Since a very high acoustic loss is desired, it may be preferable to form the backing block from polymeric particles which have been fused to form a macroscopically rigid structure having remnant tortuous permeability, as described in U.S. Pat. No. 5,297,553, assigned to the assignee of this invention. Once the structure has been laminated, individual elements are defined by dicing through the matching layers, PZT and partially into the backing block as is well known. Thereafter, the substrate can be bent to final shape.

IC multiplexers such as those described in Proudian U.S. Pat. No. 4,917,097 and Eberle U.S. Pat. No. 5,368,037 may be incorporated in the distal end of the catheter to couple the signal conductors of the ultrasonic transducer array to the electronics of the ultrasound system. Alternatively, IC multiplexers which allow a selection between the channels of the radial phased array and the channels of the linear phased array may be used thereby saving space, since when a device smaller than about 2–3 mm in diameter incorporates an ultrasonic array it may become necessary to incorporate multiplexers in the device.

Figure 6:
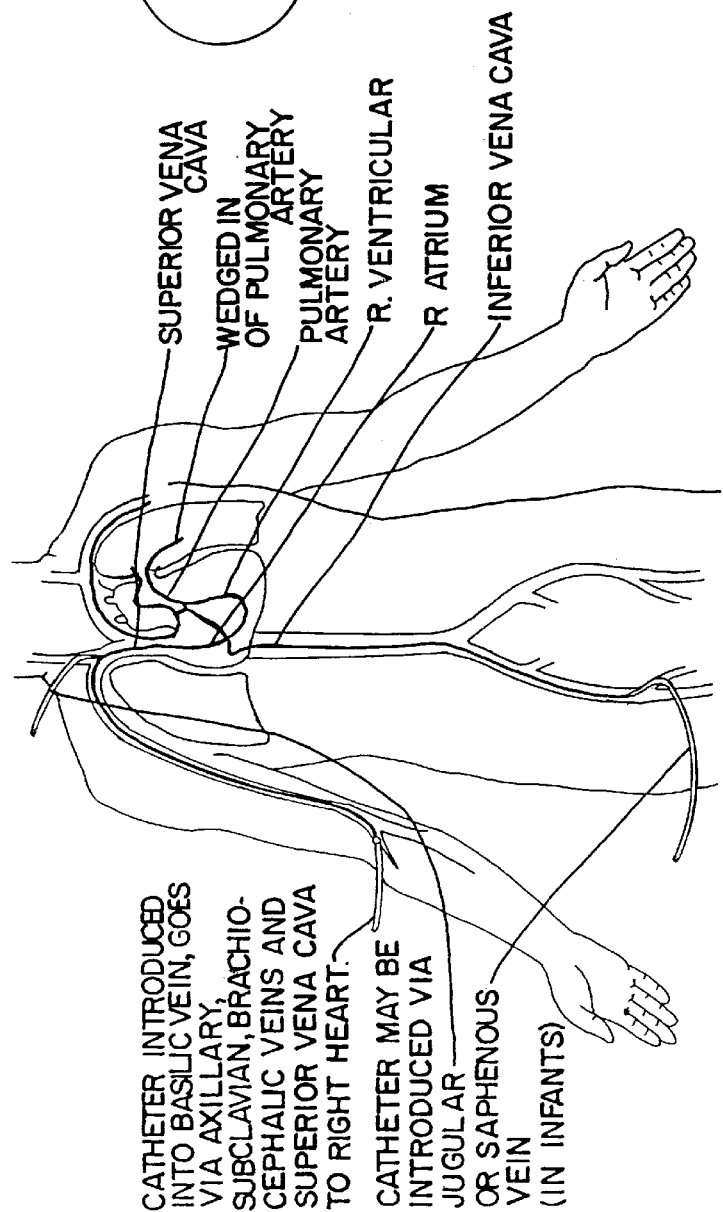
FIG. 6 is a schematic diagram illustrating a catheter inserted into a chamber of the heart of a patient.

FIG. 6 is a schematic illustrating a catheter inserted into a chamber of the heart of a patient. In the example shown in FIG. 6, the catheter is inserted into the right atrium of the patient's heart so that the radial phased array 22 can be used to image structures such as the crista terminalis and the coronary sinus orifice as well as give an indication of relative position of the catheter within the chamber. While still in the right atrium, the linear phased array 20 can be used to image the left atrium and left ventricle as well as other structures such as the mitral, tricuspid, aortic and pulmonary valves as an example. In addition, while the radial phased array 22 does not have good image resolution in the far field, it does provide a 360 degree view and outline of the heart chamber which can assist in understanding and interpreting the images obtained by the linear phased array 20. This can be very useful, for example, to an electrophysiologist who is not typically familiar with ultrasound images of the heart. The catheter is inserted into the heart by well known techniques which need not be described here in detail.

By utilizing both types of arrays 20 and 22 in one catheter, the cardiac structures in the very near field can be visualized with the radial phased array 22 and structures deeper or on the opposite side of the heart can be imaged with the linear phased array 20.

While the catheters shown in FIGS. 1–5 has the linear phased array 20 located proximal of the radial phased array 22, their positions can be reversed so that the radial phased array 22 is proximal of the linear phased array 20.

In addition, to provide good near and far field resolution, the catheters according to the preferred embodiment shown in FIGS. 1–5 can be used to reconstruct three dimensional images. More particularly, one array may be used as an imaging array and the other array may be used as a tracking array. For example, if the radial phased array is used as the imaging array and the linear phased array is used as the tracking array, multiple two dimensional image data sets are accumulated from the radial phased array as the catheter is pushed or pulled through the region of interest. The linear phased array is used for collecting frame to frame tracking data by feature tracking between successive scans using, for example, the sum of absolute differences technique. In this way the longitudinal displacement between successive radial phased scans is obtained and sufficient locating data is acquired to allow the multiple two dimensional image data sets to be assembled into a three dimensional volume.

Alternatively, if the linear phased array is used as the imaging array and the radial phased array is used as the tracking array, multiple two dimensional image data sets are acquired using the linear phased array. The catheter is rotated and the radial phased array acquires multiple data sets which are analyzed to determine the extent of rotation between frames. This provides enough locating information to allow the multiple two dimensional image data sets to be assembled into a three dimensional volume. Alternatively, both arrays 20 and 22 may be used as tracking arrays.

Image reconstruction techniques are described in greater detail in U.S. patent application Ser. No. 08/807,498, entitled "Multiple Ultrasound Image Registration System, Method, and Transducer," concurrently filed herewith (Attorney Docket No. 5050/183) which is a continuation-in-part of U.S. patent application Ser. No. 08/621,561, filed Mar. 25, 1996 which is a continuation-in-part of provisional application Ser. No. 60/012,578 filed Feb. 29, 1996, all of which are assigned to the assignee of the present invention and all of which are hereby incorporated herein by reference.

FIG. 7 is a block diagram of an ultrasonic imaging system according to a preferred embodiment of the present invention. The following discussion will first present a system overview, and then a detailed description of select components of the system.

System Overview

The system 100 includes a beamformer system/signal detector 102 which includes both transmit and receive beamformers and is connected via a multiplexer/demultiplexer 104 to the catheters shown in FIGS. 1–5. If both arrays are operating in a conventional mode where the active transducer aperture is operated simultaneously in a phased manner then any conventional device such as the Acuson XP may be used for element 102. If the arrays are being operated in a synthetic aperture mode, i.e., in which the elements of the array are operated in a sequential rather than simultaneous mode, then it is necessary for the system to store the receive element signals in a temporary store until all of the transmit-receive element combinations have been received. Once all the echo signals have been received then the data in the temporary storage registers are delayed and summed to produce a beamformed signal. Systems for implementing this type of synthetic focusing by temporarily storing single channel data until all channel data has been received are well known, for example, see Proudian U.S. Pat. No. 4,917,097. The system preferably accumulates multiple signals for each transmitter-receiver pair so that signal averaging is achieved thereby resulting in an improvement in the signal to noise ratio. Alternatively instead of using a common transducer element for both transmitter and receiver a separate receiver can be used for each transmitter channel selected. Such a method is described by O'Donnell et al. in "Synthetic Phased Array Imaging of coronary Arteries With An Intraluminal Array," Proceedings of the 1995 IEEE Ultrasonics Symposium, pp. 1251–1254 (1995). Individual elements are sequentially used as transmitters. As each element is used as a transmitter, separate adjacent elements are used as receivers on a sequential basis. In this way the array can be made to synthesize the operation of a conventional large scale phased array scanner but with the added advantage that dynamic transmit focusing as well as dynamic receive focusing is possible since the individual channel transmit path lengths are known uniquely. The low signal to noise ratio of the catheter array elements is partially overcome by averaging the successive firings of the same element pairs. Preferably, as many averages as possible are used consistent with not providing an imaging frame rate which is slower than desired by the user. Preferably the catheter array is operated with frequencies in the range of about 5 to 20 MHz. If lower frequencies are used, then the linear array has less problems with grating lobes. Alternatively, a lower frequency can be used when operating steered ultrasonic lines as describe in U.S. Pat. No. 5,549,111. When the linear phased array is used to accumulate tracking information, the array can be operated at a high frequency, for example, 20 MHz, since only a relatively small set of data is required in order to derive the motion information.

The beamformer system/signal detector 102 sends excitation signal pulses to the arrays 20 and 22 and supplies summed returning echoes to a signal detector. The output of the signal detector is supplied to a scan converter 124. The beamformer system/signal detector 102 accumulates data from the array elements in arrays 20 and 22 and forms beamformed acoustic line outputs. The scan converter 124 controls an output display 126 to display preferably the two images generated by the two arrays 20, 22. In a preferred embodiment, the output display 126 displays the views obtained from the linear phased array 20 and the radial phased array 22 simultaneously on a split screen. Alternatively, the operator may flip back and forth between views. The possible display options will be described in greater detail hereinafter.

In addition, scan-converted image information from the scan converter 124 is stored in a data storage system 128. In this preferred embodiment the data storage system 28 includes two separate storage arrays, each storing data for image frames from a respective one of the arrays 20 and 22. The catheters as described in FIGS. 1–5 include two separate transducer arrays 20 and 22. In a preferred embodiment, the linear phased array 20 is used for collecting image data that will be used to construct displayed representation of the region of interest. The radial phased array 22 operates as a tracking array. The tracking array 22 is used in this preferred embodiment to estimate the motion between respective image data frames from the image data array 20 to allow the image data frames to be registered properly for reconstruction. In another preferred embodiment, the radial phased array 22 operates as the imaging array and the linear phased array 20 operates as the tracking array. Thus, image information from the image array 20 is stored as frames of image data in the storage array 130, and image information from the tracking array 22 is stored as respective frames of tracking data in the storage array 132. The frames of data in the storage arrays 130 and 132 are all time marked, so that they can be associated with one another appropriately. This time marking can take the form of real-time clock information or frame number information, for example.

The frames of image data in the storage array 130 are applied to a computer 136. It is these frames that are used to form the displayed representation of the region of interest. The tracking frames stored in storage array 132 are not necessarily registered to create a displayed reconstruction of the region of interest but are instead used to determine the relative positions of individual frames of image data from the image data storage array 130.

In order to estimate movement of the catheter 10 between successive frames of the image data, the tracking information from the tracking array data storage array 132 is supplied to a motion estimator 138. The motion estimator 138 compares sequences of frame data from the tracking array 22 to estimate a component of motion of the catheter 10 between the respective frames. This estimate of the component of motion is smoothed in logic 140, and then applied to a calculator 142 that calculates a vector value defining the best estimate of the movement between selected frames of the data stored in the image data storage array 130. This vector is then applied as another input to the computer 136.

The computer 136 registers selected frames of image data from the image data storage array 130 with respect to one another by appropriate use of the vectors supplied by the calculator 142. Also any necessary interpolation is done, and the respective frames of image data are stored in proper registration with respect to one another in a three-dimensional data storage device 144. The computer 136, when operating in a display mode, can select appropriate information from the three-dimensional data storage device 144 to provide a desired image on the display 146. For example, cross sections can be taken in various planes, including a wide variety of planes that do not correspond to the planes of the image data. Also, surface renderings and segmentation displays can be created if desired.

Common signal conductors can be used between the beamformer/signal detector 102 and the housing for the catheter 10. In the housing, individual signals are routed between the signal conductors and the transducer elements of the arrays 20 and 22 by high voltage analog switches or multiplexers.

Angular Motion Detection

Figure 9:
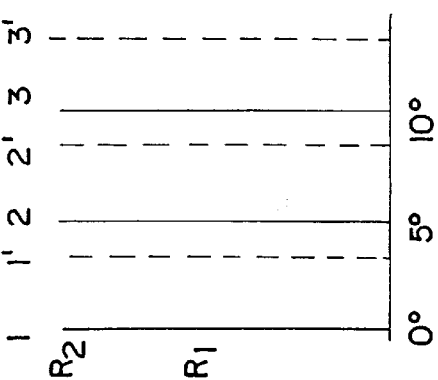
FIG. 9 illustrates the subset of beam data unwrapped.
Figure 8:
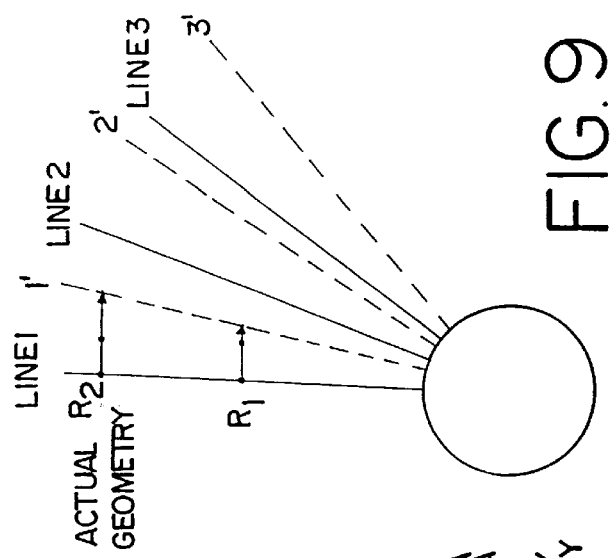
FIG. 8 illustrates a subset of beam data.

With respect to the radial array, the output of the beamformer are polar in format. For measuring rotational motion rather than Cartesian motion, it is simpler to retain the acoustic line data in polar format, i.e., not scan converted. Typically, the beamformer outputs lines are detected to form unipolar signals and are scan converted to digital quantities. FIG. 8 illustrates how a subset of beam data appears in reality, i.e. scan converted into Cartesian coordinates. It is much simpler, however, to unwrap the axial display shown in FIG. 8, i.e. do not scan convert it. FIG. 9 illustrates how this data is unwrapped to form the straight polar case. The increment between successive beam lines is simply their angular separation, for example, 5 degrees. With respect to detecting the motion of pixel values from Line 1 to Line etc., it is evident that by using polar coordinates the correct answer for rotation is arrived at more simply.

Display Options

Since one is able collect image data from both arrays and use one or both sets for tracking motion of the other plane, various display options exist.

Figure 10:
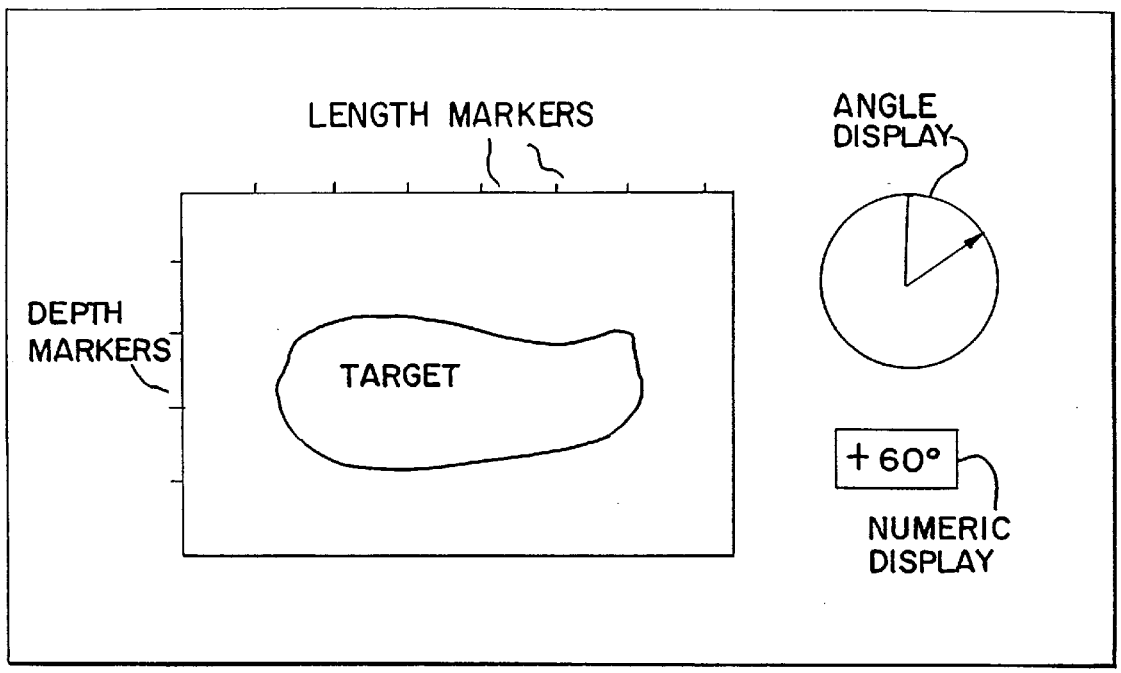
FIG. 10 illustrates a display of the linear phased array according to a preferred embodiment of the present invention.

FIG. 10 illustrates a display of the linear phased array. The angle of probe rotation with respect to some user defined arbitrary starting point has been measured. This angle is an indication of the relative angular direction of the image frame produced by the linear phased array and may be displayed as a circular icon as shown in FIG. 10 and/or a numeric output as is also displayed. The circular icon assumes that the user defined origin is at the top of the circle (for example) and the angular rotation of the probe with respect to this position is shown by an arrow suitably angled with respect to the starting point, i.e., the top of the circle. Software for displaying such icons is well within the scope of those skilled in the art.

Figure 11:
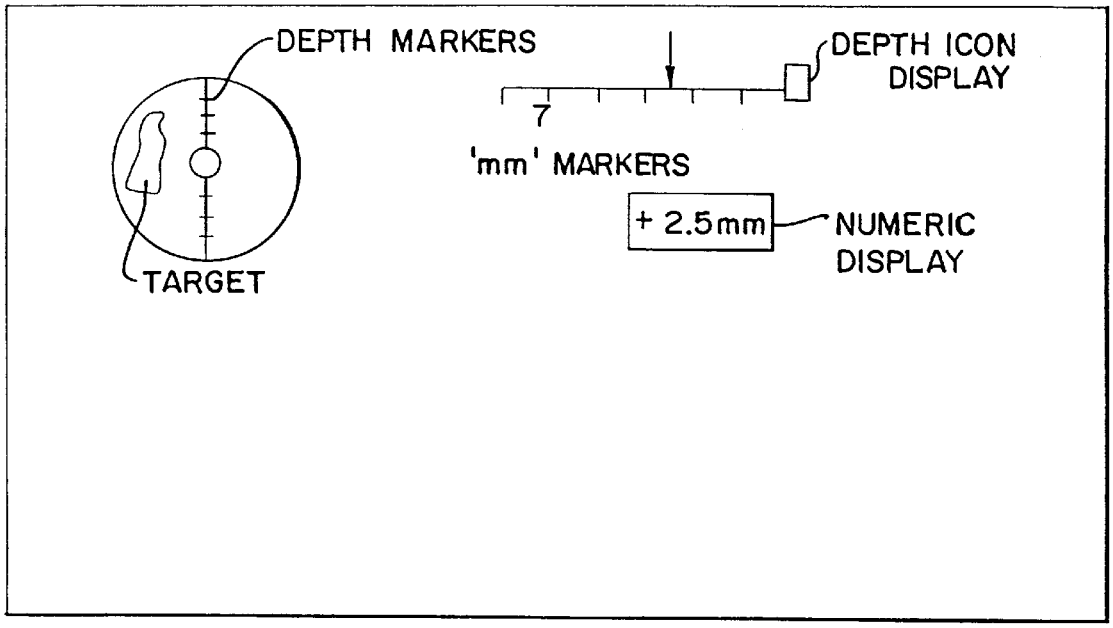
FIG. 11 illustrates a display of the radial phased array according to a preferred embodiment of the present invention.

FIG. 11 illustrates a display of the radial phased array. The radial display is presented and depth of penetration as detected by motion sensed from the linear array is also displayed. Again the reference point for the start of motion detection is arbitrary and the user should have the option of resetting it by, for example, selection of a key on a keyboard. An icon display for the detected depth relative to the last resetting of the depth measurement is also shown in FIG. 11. Preferably the icon is in the form of a ruler like object with an arrow pointing to the current position. Optionally, a numeric display indicating millimeters of penetration is also provided.

Figure 12:
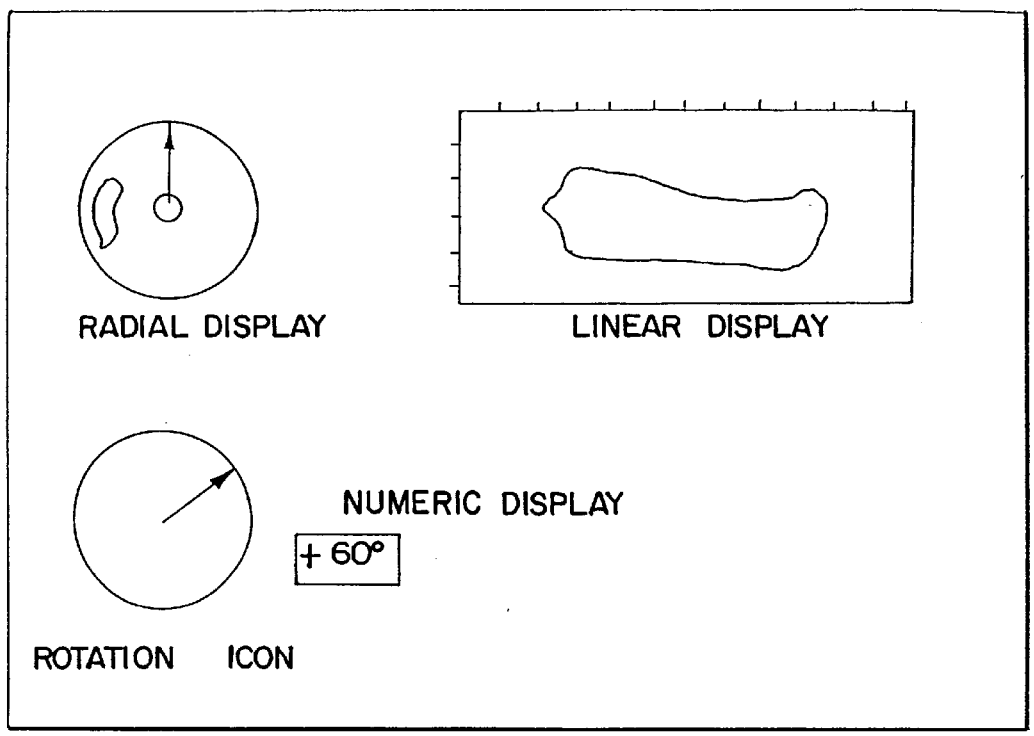
FIG. 12 illustrates a display of images from both the linear phased array and the radial phased array according to a preferred embodiment of the present invention.

FIG. 12 illustrates a display of images from both the linear phased array and the radial phased array. In the embodiment shown in FIG. 12 both the radial and linear array images are displayed each having tick marks indicating a scale in either mm or cm. Preferably the scan converter sets the millimeter scales to be equal in dimension in both displays. Displaying multiple ultrasound images is relatively well known, for example, simultaneous B-Mode and M-Mode. In this case an angle display is also provided which indicates the present position of the linear array image with respect to the last resetting of the angle measurement.

Figure 13:
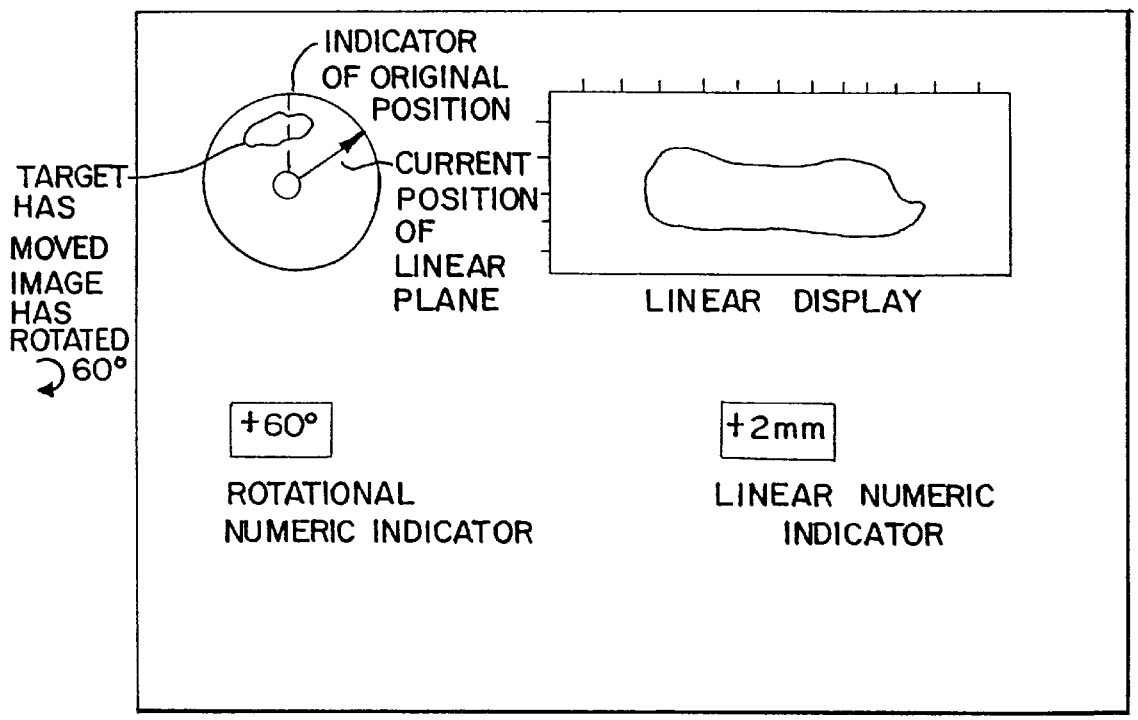
FIG. 13 illustrates a display of images from both the linear phased array and the radial phased array according to a preferred embodiment of the present invention.

FIG. 13 illustrates a display of images from both the linear phased array and the radial phased array. In this preferred embodiment the radial image display is rotated according to the detected rotation angle such that the display rotation completely compensates for the physical device rotation. Thus, the image appears to remain static though the image is moving with respect to the array. If the system detects that an arbitrary object has moved 20 degrees anticlockwise, the system signals the scan converter to rotate the image 20 degrees clockwise to compensate. The concept of the detecting image motion and altering the display to correct for it is described in considerable detail in Bamber U.S. Pat. No. 5,538,004.

Figure 14:
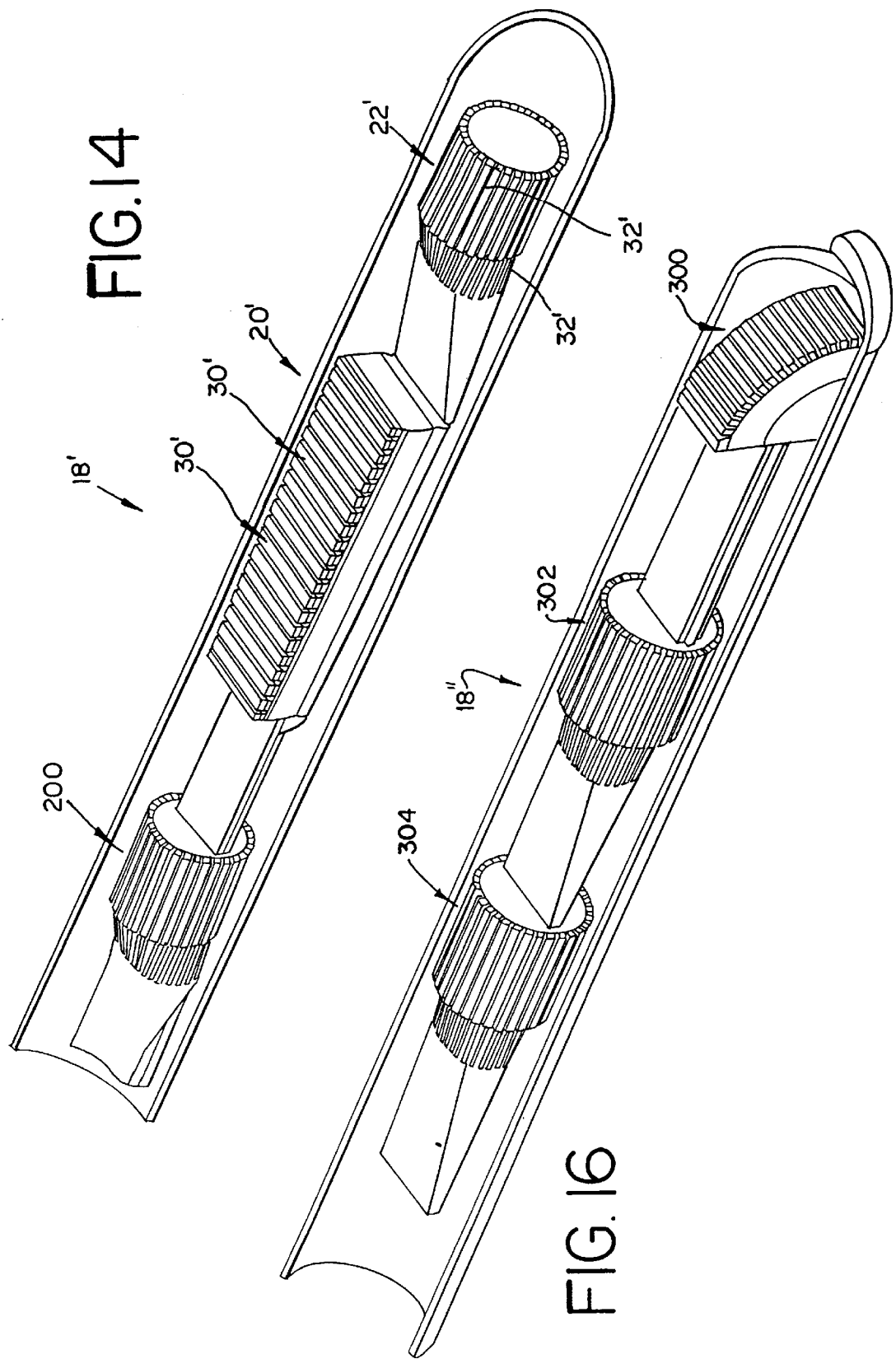
FIG. 14 illustrates the distal end region of another preferred embodiment of a catheter according to the present invention.
Figure 15:
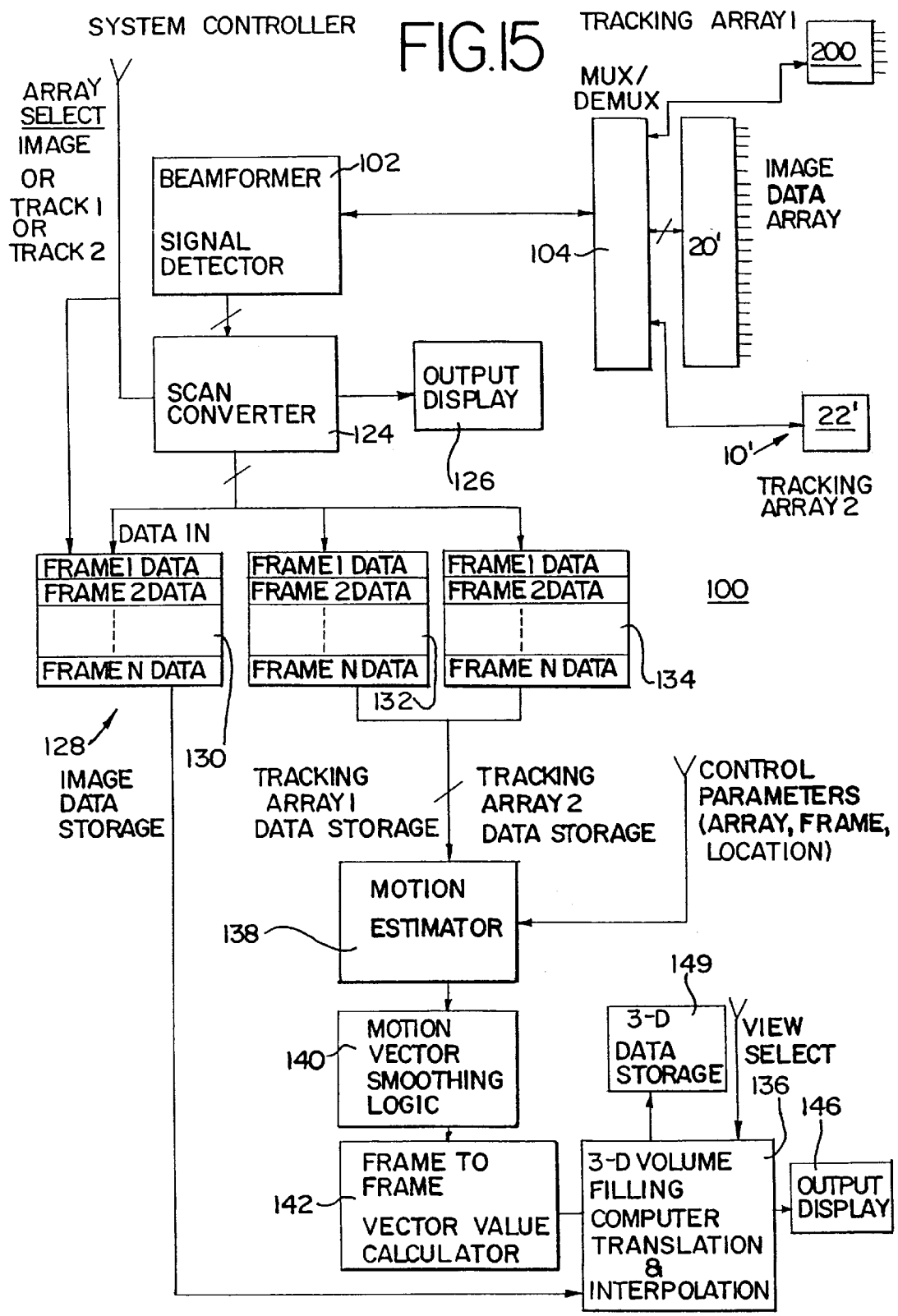
FIG. 15 illustrates an ultrasonic system according to a preferred embodiment in which catheter such as that shown in FIG. 14 includes two tracking arrays.

FIG. 14 illustrates the distal end region 18' of another preferred embodiment of a catheter according to the present invention. A second radial array 200 is included on the opposite end of the linear array 20'. The second radial array may extend 360° or it may extend less than 360°. FIG. 15 illustrates an ultrasonic system according to a preferred embodiment in which a catheter such as that shown in FIG. 14 includes two tracking arrays.

FIG. 16 illustrates the distal region 18" of still another preferred embodiment of a catheter according to the present invention. In this preferred embodiment a curved linear phased array 300 is disposed distal of the first radial phased array 302 and is curved. Optionally a second radial phased array 304, shown may be provided proximal of the first radial phased array 302.

If desired, the catheter can include an absolute sensor for position, orientation, or both, such as a magnetic sensor or an accelerometer. The sensor 19 may be used to supplement or back up the motion detection approach and may be of the types described in Kelier U.S. Pat. No. 5,353,354 or one of the smaller sensors manufactured by Biosense, Inc. of Setauket, N.Y.

While this invention has been shown and described in connection with the preferred embodiments, it is apparent that certain changes and modifications, in addition to those mentioned above, may be made from the basic features of the present invention. Accordingly, it is the intention of the Applicant to protect all variations and modifications within the true spirit and valid scope of the present invention.

What is claimed is:

1. An ultrasonic catheter comprising:
   a body having a longitudinal axis, a circumference and a distal end region;
   a first ultrasonic transducer array disposed in the distal end region of the body; and
   a second ultrasonic transducer array disposed in the distal end region of the body.

2. An ultrasonic catheter according to claim 1 wherein the first ultrasonic array is a linear phased array and the second ultrasonic array is a radial phased array.

3. An ultrasonic catheter according to claim 2 wherein the linear phased array has an azimuth that is parallel to the longitudinal axis of the body.

4. An ultrasonic catheter according to claim 2 wherein the linear phased array is disposed proximal of the radial phased array.

5. An ultrasonic catheter according to claim 2 further comprising a third ultrasonic array wherein the third ultrasonic array is a second radial phased array which is separated from the radial phased array along the longitudinal axis of the body.

6. An ultrasonic catheter according to claim 5 wherein the linear phased array is disposed between the radial phased array and the second radial phased array.

7. An ultrasonic system comprising:
   an ultrasonic catheter comprising a body having a longitudinal axis, a circumference and a distal end region, a first ultrasonic transducer array disposed in the distal end region of the body, and a second ultrasonic transducer array disposed in the distal end region of the body; and
   a transmit beamformer and a receive beamformer coupled to each of the first and second ultrasonic transducer arrays.

8. An ultrasonic system according to claim 7 wherein the first array is a linear phased array and the second array is a radial phased array.

9. An ultrasonic catheter according to claim 2 wherein the linear phased array has a plurality of transducer elements sequentially disposed along the longitudinal axis of the body.

10. An ultrasonic catheter according to claim 2 wherein the linear phased array is curved around a distal most point of the distal end region of the body.

11. An ultrasonic system according to claim 7 further comprising a display system coupled to the transmit and receive beamformers to display the acquired image frames from the first and second arrays.

12. An ultrasonic system according to claim 7 further comprising a computer coupled to the transmit and receive beamformers wherein the computer is programmed to (1) acquire a plurality of sets of two-dimensional image data in an image plane generated by the first array upon excitation by the transmit beamformer, the first array moved between acquisition of at least some of the sets of image data (2) acquire two-dimensional tracking data in one tracking plane oriented at a non-zero angle with respect to the image plane with the second array upon excitation by the transmit beamformer, the second array moved between acquisition of at least some of the sets of tracking data; (3) automatically determine a component of motion based on a comparison of at least a portion of the tracking sets acquired in step (2), and (4) automatically use the component of motion determined in step (3) to register select ones of the image data acquired in step (1).

13. An ultrasonic system according to claim 12 wherein the first array is a linear phased array and the second array is a radial phased array.

14. An ultrasonic system according to claim 12 wherein the first array is a radial phased array and the second array is a linear phased array.

15. A method for registering image information acquired from an interior region of a patient, said method comprising the steps of:
   (a) inserting a catheter into a patient to image an interior region of the patient, the catheter having a body having a longitudinal axis, a circumference and a distal end region, a first ultrasonic transducer array disposed in the distal region of the body and a second phased ultrasonic transducer array disposed in the distal end region of the body;
   (b) acquiring a plurality of sets of image data in an image plane with the first ultrasonic transducer array, the first ultrasonic transducer array moved between acquisition of at least some of the sets of image data;
   (c) acquiring a plurality of sets of tracking data in a tracking plane oriented at a non-zero angle with respect to the image plane with the second ultrasonic transducer array, the second ultrasonic transducer array moved between acquisition of at least some of the sets of tracking data;
   (d) automatically determining a component of motion based on a comparison of at least a portion of the tracking sets acquired in step (c); and
   (e) automatically using the component of motion determined in step (d) to register select ones of the image data sets acquired in step (b).

16. The method of claim 15 wherein the step (d) comprises the step of correlating the tracking data sets acquired in step (c).

17. The method of claim 15 wherein the first image information comprises information selected from the group consisting of B mode information, color Doppler velocity information, color Doppler energy information, and combinations thereof.

18. The method according to claim 15 wherein the step of moving the first and second ultrasonic transducer arrays comprises rotating the catheter.

19. The method according to claim 15 wherein the step of moving the first and second ultrasonic transducer arrays comprises translating the catheter in a direction parallel to the longitudinal axis.

20. A method for imaging a cardiac structure, the method comprising the steps of:
   (a) inserting a catheter having a body having a longitudinal axis, a circumference and a distal end region with a first phased ultrasonic transducer array and a second phased ultrasonic transducer array disposed thereon;
   (b) acquiring image information from the first phased ultrasonic transducer array; and
   (c) acquiring image information from the second phased ultrasonic transducer array.

21. A method according to claim 20 further comprising the step of displaying the image information acquired in steps (b) and (c) on a display unit.

22. A method according to claim 21 wherein the image information acquired in steps (b) and (c) are simultaneously displayed.

23. A method according to claim 21 wherein the image information acquired in steps (b) and (c) are sequentially displayed.

24. A method for registering image information acquired from an interior region of a patient, said method comprising the steps of:
 (a) inserting an catheter having a body having a longitudinal axis, a circumference and a distal end region, a linear phased ultrasonic transducer array disposed in the distal region of the body and a first radial phased ultrasonic transducer array disposed around the circumference of the distal end region of the body into a patient to image an interior region of the patient;
 (b) acquiring first two-dimensional image information in an image plane with the radial phased ultrasonic transducer array;
 (c) acquiring tracking two-dimensional data information in a tracking plane oriented at a non-zero angle with respect to the image plane with the linear phased ultrasonic transducer array;
 (d) repeating steps (b) and (c) after moving the catheter along a direction having a component of motion in the tracking plane;
 (e) automatically determining the component of motion based on a comparison of the tracking two-dimensional data information acquired in steps (c) and (d); and
 (f) automatically using the component of motion determined in step (e) to register the first image information acquired in step (d) with the first image information acquired in step (b).

25. The method of claim 24 wherein step (e) comprises the step of correlating the tracking two-dimensional information acquired in steps (c) and (d).

26. The method of claim 24 wherein the first image information comprises information selected from the group consisting of B mode information, color Doppler velocity information, color Doppler energy information, and combinations thereof.

27. An ultrasonic catheter according to claim 2 wherein the radial array is an annular array.

28. An ultrasonic catheter according to claim 2 wherein the radial array is a curved linear phased array.

29. An ultrasonic catheter according to claim 2 wherein the radial array is a planar linear phased array.

30. An ultrasonic catheter according to claim 5 wherein the radial phased array and second radial phased array are annular arrays.

31. An ultrasonic catheter according to claim 5 wherein the radial phased array is an annular array and the second radial phased array is a curved linear phased array.

32. An ultrasonic catheter according to claim 5 wherein the linear phased array is a curved array.

33. An ultrasonic catheter according to claim 6 wherein the radial phased array and the second radial phased array are annular arrays.

34. An ultrasonic catheter according to claim 6 wherein the radial phased array is an annular array and the second radial phased array is a curved linear phased array.

35. An ultrasonic catheter according to claim 2 wherein the linear phased array is disposed distal of the radial phased array.

36. An ultrasonic catheter according to claim 35 wherein the radial phased array is an annular array.

37. An ultrasonic catheter according to claim 36 wherein the linear phased array is a curved array.

38. An ultrasonic catheter according to claim 35 further comprising a second radial phased array disposed in the distal end region of the body.

39. An ultrasonic catheter according to claim 38 wherein the second radial phased array is disposed proximal of the radial phased array.

40. An ultrasonic catheter according to claim 39 wherein the radial phased array and second radial phased array are annular arrays.

41. An ultrasonic system according to claim 12 further comprising a display system coupled to the transmit and receive beamformers to display the two-dimensional image information and the component of motion determined in step (3).

42. An ultrasonic catheter according to claim 12 further comprising the steps of repeating steps (1), (2) and (3) and accumulating the component of motion determined in step (3) to generate a composite detected motion wherein the composite detected motion indicates the motion of the catheter with respect to a predetermined reference point.

43. An ultrasonic system according to claim 41 wherein the first array is a linear phased array and the second array is a radial phased array.

44. An ultrasonic system according to claim 43 wherein the composite detected motion is illustrated as a circular icon with an arrow indicating the degree of rotation from a reference point.

45. An ultrasonic system according to claim 44 further comprising a numerical display of the composite detected motion.

46. An ultrasonic system according to claim 44 wherein the computer is further programmed to acquire two-dimensional image information in an image plane generated by the second array upon excitation by the transmit beamformer and the display system displays the two-dimensional image information generated by the second array.

47. An ultrasonic system according to claim 46 wherein the circular icon is displayed over the two-dimensional image information generated by the second array.

48. An ultrasonic system according to claim 47 wherein the position of the two-dimensional image information changes according to the composite detected motion.

49. An ultrasonic system according to claim 41 wherein the first array is a radial phased array and the second array is a linear phased array.

50. An ultrasonic system according to claim 49 wherein the composite detected motion is illustrated as a ruler icon with an arrow indicating the degree of translation from a reference point.

51. An ultrasonic system according to claim 50 further comprising a numerical display of the composite detected motion.

52. An ultrasonic system according to claim 50 wherein the computer is further programmed to acquire two-dimensional image information in an image plane generated by the second array upon excitation by the transmit beamformer and the display system displays the two-dimensional image information generated by the second array.

53. An ultrasonic system according to claim 52 wherein the ruler icon is displayed over the two-dimensional image information generated by the second array.

54. An ultrasonic system according to claim 53 wherein the position of the two-dimensional image information compensates for the composite detected motion.

55. The method of claim 15 further comprising the steps of:
 (f) repeating steps (b), (c), and (d) and accumulating the component of motion detected in step (d) to generate composite detected motion wherein the composite detected motion indicates the motion of the catheter with respect to a predetermined reference point;

(g) displaying the two-dimensional image data acquired in step (b); and (h) displaying the composite detected motion determined in step.

56. The method according to claim 55 wherein the step of displaying the composite detected of motion comprises displaying an icon representation of the composite detected motion.

57. The method according to claim 56 wherein the second array is a radial phased array and the icon is a circle with an arrow indicating the degree of rotation.

58. The method according to claim 56 wherein the second array is a linear phased array and the icon is a ruler with an arrow indicating the degree of translation.

59. The method according to claim 55 further comprising the step of (i) acquiring two-dimensional image information in the tracking plane with the second array; and (j) displaying the two-dimensional image information acquired in step (i).

60. The method according to claim 59 wherein the step of displaying the composite detected motion comprises displaying an icon representative of the composite detected motion.

61. The method to claim 60 wherein the icon is displayed over the two-dimensional image information displayed in step (j).

62. The method according to claim 55 wherein the step of displaying the composite detected motion comprises displaying a numerical value representative of the composite detected motion.

63. A method according to claim 20 wherein the first array is a linear phased array and the second array is a radial phased array.

64. A method according to claim 63 wherein the radial phased array is an annular array.

65. An ultrasonic system according to claim 12 further comprising a display system coupled to the transmit and receive beamformers to display a three-dimensional image.

66. The method of claim 15 further comprising the step of displaying a three-dimensional image.

67. An ultrasonic catheter according to claim 1 further comprising a position/orientation sensor disposed in the distal end region of the body.

68. An ultrasonic catheter according to claim 67 wherein the sensor is a magnetic sensor.

69. An ultrasonic catheter according to claim 1 wherein the first and second ultrasonic transducer arrays are each coupled to a transmit beamformer and a receive beamformer, and a processor is coupled to the transmit and receive beamformers wherein the processor is programmed to (1) acquire two-dimensional image information in an image plane generated by the first array upon excitation by the transmit beamformer, (2) acquire tracking two-dimensional data information in one tracking plane oriented at a non-zero angle with respect to the image plane with the second array upon excitation by the transmit beamformer; (3) repeat steps (1) and (2) after the catheter has been moved along a direction having a component of motion in the tracking plane (4) determine the component of motion based on a comparison of the tracking two-dimensional data information acquired in steps (2) and (3), and (5) use the component of motion determined in step (4) to register the first image information acquired in step (3) with the image information acquired in step (1).

70. An ultrasonic catheter according to claim 69 wherein the first array is a linear phased array and the second array is a radial phased array.

71. An ultrasonic catheter according to claim 69 wherein the first array is a radial phased array and the second array is a linear phased array.

72. An ultrasonic catheter according to claim 69 wherein the processor is coupled to a display wherein the two-dimensional image information acquired in step (1) and the component of motion determined in step (4) can be displayed.

73. An ultrasonic catheter according to claim 69 wherein the processor is programmed to acquire two-dimensional image information with the second array and wherein the processor is coupled to a display wherein two-dimensional image information acquired from at least one of the first and second arrays can be displayed.

74. An ultrasonic catheter according to claim 69 wherein the processor is coupled to a display and the processor is programmed to form a three-dimensional reconstruction and wherein the three-dimensional reconstruction is displayed.

75. An ultrasonic catheter according to claim 1 wherein the first and second ultrasonic transducer arrays are coupled to a transmit beamformer and a receive beamformer, and a processor and a display are coupled to the transmit and receive beamformers, wherein the processor is programmed to (1) acquire two-dimensional image information in a first image plane generated by the first array upon excitation by the transmit beamformer, (2) acquire two-dimensional image information in a second image plane generated by the second array upon excitation by the transmit beamformer, and (3) selectively display the two-dimensional image information acquired from at least one of the first or second arrays.

\* \* \* \* \*

UNITED STATES PATENT AND TRADEMARK OFFICE
CERTIFICATE OF CORRECTION

PATENT NO. : 5,876,345
DATED : March 2, 1999
INVENTOR(S) : John W. Eaton et al.

It is certified that error appears in the above-identified patent and that said Letters Patent is hereby corrected as shown below:

<u>On the Title Page</u> item [54], and column 1, line 2, change "TWO DIMENSIONAL" to --TWO-DIMENSIONAL--.

In column 2, line 1, under "OTHER PUBLICATIONS", change "Rosenfiedl" to --Rosenfield--.

In column 2, line 4, under "OTHER PUBLICATIONS", change "Corculation" to --Circulation--.

In column 2, line 20, under "OTHER PUBLICATIONS", change "Echocardiogrphy" to --Echocardiography--.

On Page 2, column 2, line 1, under "OTHER PUBLICATIONS", change "Three Dimensional" to --Three-Dimensional--.

In column 5, line 19, after "annulus" insert --circle--.

In column 5, line 25, after "axis of the" insert --probe--.

In column 6, line 56, change "has" to --have--.

UNITED STATES PATENT AND TRADEMARK OFFICE
CERTIFICATE OF CORRECTION

PATENT NO. : 5,876,345
DATED : March 2, 1999
INVENTOR(S) : John W. Eaton et al.

It is certified that error appears in the above-identified patent and that said Letters Patent is hereby corrected as shown below:

In column 7, line 65, change "coronary" to --Coronary--.

In column 9, line 52, before "etc." insert --1'--.

In column 10, line 61, change "Kelier" to --Keller--.

In claim 55, line 11, after "step" insert --(d)--.

In claim 56, line 2, delete "of".

Signed and Sealed this

Twenty-sixth Day of September, 2000

Attest:

Q. TODD DICKINSON

*Attesting Officer*   *Director of Patents and Trademarks*